United States Patent [19]

Byrne et al.

[11] Patent Number: 5,588,437
[45] Date of Patent: Dec. 31, 1996

[54] BLOOD FLOW DETERMINATION

[75] Inventors: Phillip O. Byrne; Timothy J. H. Essex, both of Newcastle Upon Tyne, England

[73] Assignee: British Technology Group Limited, London, England

[21] Appl. No.: 197,442

[22] Filed: Feb. 16, 1994

Related U.S. Application Data

[63] Continuation of Ser. No. 768,862, filed as PCT/GP90/00459, Mar. 28, 1990, abandoned.

[30] Foreign Application Priority Data

Mar. 29, 1989 [GB] United Kingdom .................. 8907101

[51] Int. Cl.$^6$ ...................................... A61B 5/02
[52] U.S. Cl. .................... 128/691; 128/664; 128/665
[58] Field of Search .................... 128/633, 653.1, 128/664–667, 691, 693; 356/39–42, 27, 28

[56] References Cited

U.S. PATENT DOCUMENTS

| | | |
|---|---|---|
| 3,724,932 | 4/1973 | Cornsweet et al. . |
| 4,109,647 | 8/1978 | Stern et al. ............................... 356/28 |
| 4,579,430 | 4/1986 | Bille . |
| 4,641,668 | 2/1987 | Namekawa . |
| 4,862,894 | 9/1989 | Fuji . |
| 5,081,998 | 1/1992 | Yelderman et al. ..................... 128/664 |
| 5,115,137 | 5/1992 | Anderson-Engels et al. .......... 128/633 |

FOREIGN PATENT DOCUMENTS

| | | |
|---|---|---|
| 0100094 | 2/1984 | European Pat. Off. . |
| 0282210 | 9/1988 | European Pat. Off. . |
| 2537428 | 6/1984 | France . |
| 2021759 | 12/1979 | United Kingdom . |
| 1564315 | 4/1980 | United Kingdom . |
| 2069284 | 8/1981 | United Kingdom . |
| 2170972 | 8/1986 | United Kingdom . |
| 9106344 | 5/1991 | WIPO . |
| 9106244 | 5/1991 | WIPO .................................. 128/691 |

OTHER PUBLICATIONS

Rushmer, "Blood Flow Measurement: Future Applications and Prospects"; Medical Instrumentation; 1977, pp. 170–173.

Fairs et al; "Limb Perfusion in the Lower Limb Amputee–a Comparative Study Using a Laser Doppler Flowmeter and a Transcutaneous Oxygen Electrode"; Prosthetics and Orthotics International; 1987, pp. 80–84.

P. C. Williams, et al, Mapping Of Cerebral Cortical Strokes in Rhesus Monkeys By Laser Doppler Spectroscopy, vol. 13, No. 2, dated 1980, pp. 4–5.

*Primary Examiner*—John G. Weiss
*Assistant Examiner*—P. Zuttarelli
*Attorney, Agent, or Firm*—Cushman, Darby & Cushman

[57] ABSTRACT

A method of determination of blood flow including projecting a beam (B) of laser generated light (L) to move (SM) over a surface (T) beneath which blood flow in a vessel or vascular bed is to be determined, collecting (RD)light returning scattered from the beam by the surface and by blood flowing beneath, measuring a spectrum of frequencies in said collected light, determining (DA),(F) from differences in said frequencies blood flow (VS) in a vessel or vascular bed beneath said surface. A reference for the detected frequencies is provided by light returned from the surface. A map of blood flow in a false-colour flow scale can be displayed(DU).

19 Claims, 3 Drawing Sheets

BLOOD FLOW DETERMINATION

This is a continuation of application Ser. No. 07/768,862, filed as PCT/GB90/00459, Mar. 28, 1990, which was abandoned.

BACKGROUND OF THE INVENTION

1. Field of the Invention

This invention relates to the non-invasive determination of blood flow.

2. Description of the Prior Art

In medical practice it is often essential that the pattern of blood flow be determined quickly and accurately for example, in trauma where a limb may have been reattached, the assessment of pressure sores, plastic surgery for monitoring graft viability and in peripheral vascular diseases. When amputation is likely it is important that the extent of blood flow be known.

Various techniques for blood flow determination have been proposed. One publication, "Blood Flow Measurement: Future Applications and Prospects", Robert F. Rushmer, Medical Instrumentation Vol. 11 No. 3 May-June 1977, mentions the laser-Doppler method in which a optical-Fiber directs light from a laser at the superficial vessels of the skin and reflected light indicates blood flow in these vessels. A much more recent publication, "Limb Pertusion in the Lower Limb Amputee", S.L.E. Fairs et al., Prosthetics and Orthotics International, 1987, Vol. 11 80–84, refers to the use and value of the optical-Fiber instrument but mentions problems resulting from the movement of the optical-Fiber, which has to be close to the surface of the area being examined.

SUMMARY OF THE INVENTION

It is an object of the present invention to provide a technique for the determination of blood flow which overcomes such problems. In particular it Is an object of the present invention to provide a technique by which a map of blood flow over a given area can be produced.

According to the invention there is provided a method of determination of blood flow including:

projecting a beam of laser generated light to move over a surface beneath which blood flow in a vessel or vascular bed is to be determined, collecting light returning scattered from the beam by the surface and scattered by blood flowing beneath, measuring a spectrum of frequencies in said collected light, and determining from differences in said frequencies blood flow in a vessel or vascular bed beneath said surface.

According to the invention there is provided a method of determination of blood flow including:

generating and projecting a beam of laser light, causing said beam of light to move over a surface beneath which blood flow In a vessel or vascular bed is to be determined, collecting light returned scattered from the beam by the surface and by blood flowing beneath, detecting scatter-related frequencies in said collected light, and determining from said frequencies blood flow in a vessel or vascular bed beneath said surface.

The blood flow determined in this way may be presented as an image of the surface coloured or shaded in accordance with a scale of blood flow. Light returned from the surface may provide a reference for the determination of blood flow beneath the surface. Thus a map of blood flow for a given area can be produced.

According to the invention there is provided an apparatus to determine blood flow including a low-noise laser, means to direct a beam of light from said laser to a target, means to scan the directed beam over said target, means to collect light from the beam returned from said target, means to detect frequencies in said collected returned light, means responsive to the action of the means to scan said beam and to detect collected light frequencies to determine localized target velocity information related to the position of the scan on the target and to provide said information as a scan-based signal.

The apparatus may include means to present said scan-based information as an image of localized velocity information for the target. The velocity information may be presented as information about blood flow below the surface of the target, which may be presented as a false-color image of blood flow The means to detect returned light may be an array of detectors. The beam from the laser may be directed to pass through an aperture in the array to a path also used for the returned light. The returned light frequencies may include those representing overall movement of the target and these may provide a reference for the determination of localized velocity information.

The means to scan the directed beam may include means to drive a mirror directing the beam in a steady swinging motion and in a stepwise tilting motion.

BRIEF DESCRIPTION OF THE DRAWINGS

Embodiments of the invention will now be described with reference to the accompanying drawings in which.

DETAILED DESCRIPTION OF THE PRESENTLY PREFERRED EXEMPLARY EMBODIMENT

Figure 1:
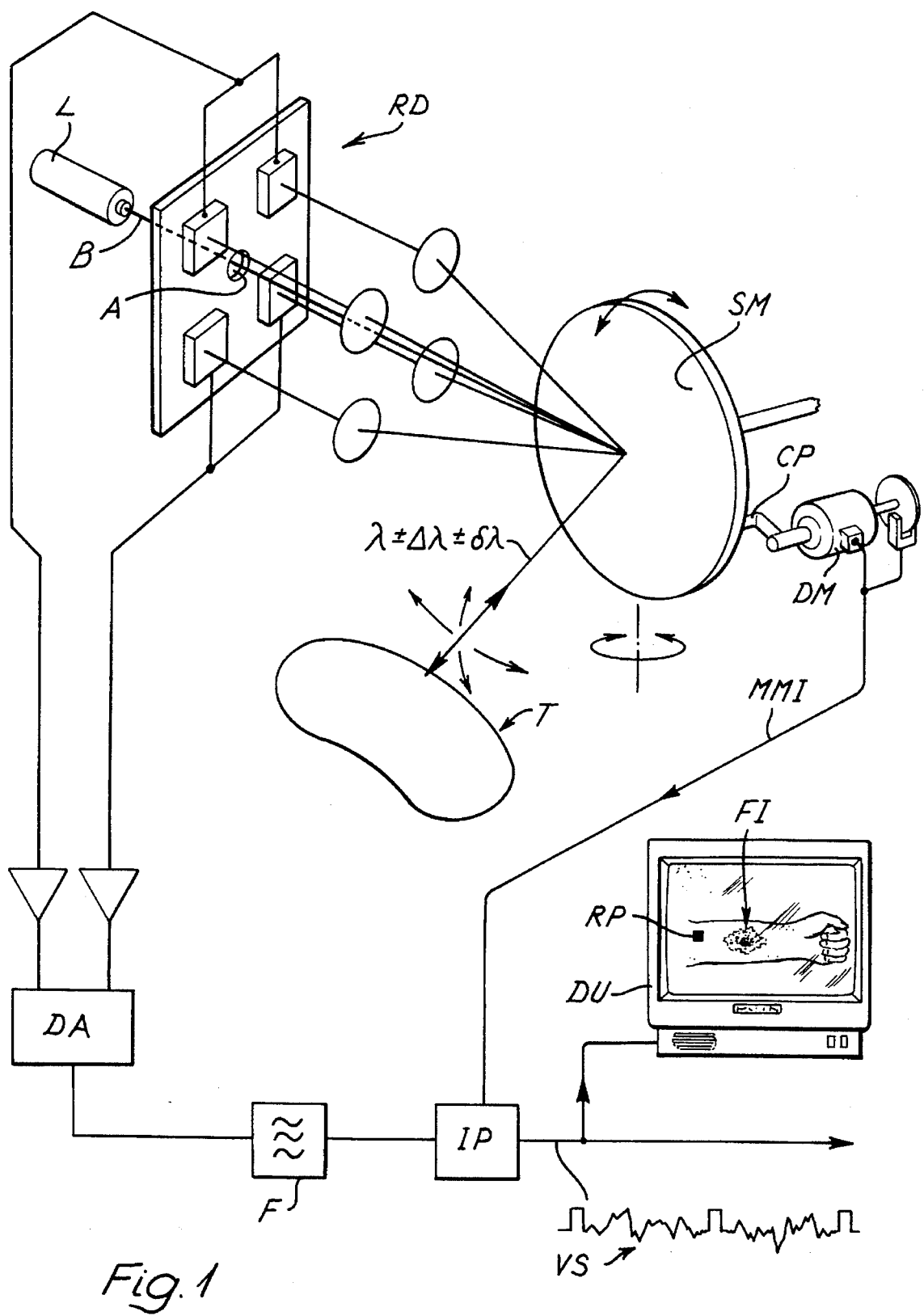
FIG. 1 is an outline schematic drawing of a scanning apparatus.

As shown in FIG. 1,2 beam of light, B, from a low-power low-noise laser, L, is directed to be reflected by a movable mirror, SM. Mirror SM is a flat mirror movable in a controlled manner to scan the laser beam B reflected from mirror SM over an object of interest such as a target T, as indicated by the curved arrows. Light returned from the target is captured by the movable mirror SM and directed to a receiving device RD. Receiving device RD is arranged so that light from the laser passes through an aperture A in the device and collected light falls on the device. Conveniently the device RD is four photo detectors such as diodes arranged in a square array. Each device has a lens or other optical device to improve the incidence of collected returned light on the receiving device.

The mirror SM is driven to swing about a generally vertical axis by a drive motor DM and linkage to produce a specific motion which is monitored in any convenient manner such as a shaft position encoder to produce a mirror motion information signal MMI. A suitable linkage is described below. The mirror SM is driven to tilt about a generally horizontal axis by a lead screw and stepping motor arrangement (not shown). A suitable construction will be readily apparent to those skilled in the art. By a suitable control arrangement, such as a microprocessor or other electronic circuitry, the stepper motor is driven a selected number of steps at the end of each swing about the vertical axis to produce a "raster" scan of the laser beam over the object. Information about the swing of the mirror about the horizontal axis can be provided as part of the signal MMI or otherwise as convenient.

The light returned from the target includes optical frequencies spread over a range from the optical frequency ($\lambda$) of the light of the beam B by scattering action. This light is collected and directed to the receiving device.

The receiving device RD and associated circuitry produce an output signal related to the shift ($\delta\lambda$) of the optical frequency of the scattered light from that of beam B, which shift results from small movements within the target, such as blood flow. A reference signal is provided by the shifted frequencies of light ($\lambda\pm\Delta\lambda$) scattered by the target as a whole, rather than beam B itself, so that movements of the target as a whole can be cancelled out.

The output signal is processed in suitable electronic circuits. The circuits to process the signal from the receiving device RD conveniently include firstly two analog amplifiers, one for the two upper diodes and the other for the two lower ones, followed by a differential amplifier DA and then a filter F. This filter has a response by which the output is proportional to frequency so as to extract the scatter-related information, represented by the $\delta\lambda$ component, resulting from blood flow motion.

In one arrangement by use of the information on the vertical and horizontal scanning mirror movement, for example from signal MMI, a video type signal VS representing the difference frequency reflected from specific parts of the object can be produced In image processor IP and an image displayed or recorded in a known manner to represent the small movements at or within the target.

In FIG. 1 a display unit DU responds to signal VS to provide an image IA of part or all of a target and, by way of example, a forearm is shown. On image IA a reference patch is indicated at RP and the shaded area FI is a flow image which can show in "false color" the blood flow pattern with greater movement colored differently from lesser movement in a range of distinct movement values. Clearly to form the image from signal VS suitable signal processing may be required. For example the signal may have to be stored until a complete frame has been covered by the scanning process. Storage and processing can be in a suitably arranged microprocessor or other equipment.

In the specific use to determine blood flow pattern in a body such an image shows distinctly areas in which blood flow is more than in others. Light returned scattered from the skin gives the information about the movement of the body as a whole and enables the removal of information that could confuse the image. In this way the effect of body movement can be cancelled or overcome.

By use of different laser colors (wavelengths) for beam B it is possible to distinguish between blood flow close to the surface of a body (green light) and flow some 2 millimeters below the surface (infrared light). This is believed to be adequate to determine all relevant blood flow and to be more useful than present imaging techniques which are not depth selective to this degree.

The proper movement of the mirror SM is important to the effective performance of the technique.

Figure 2:
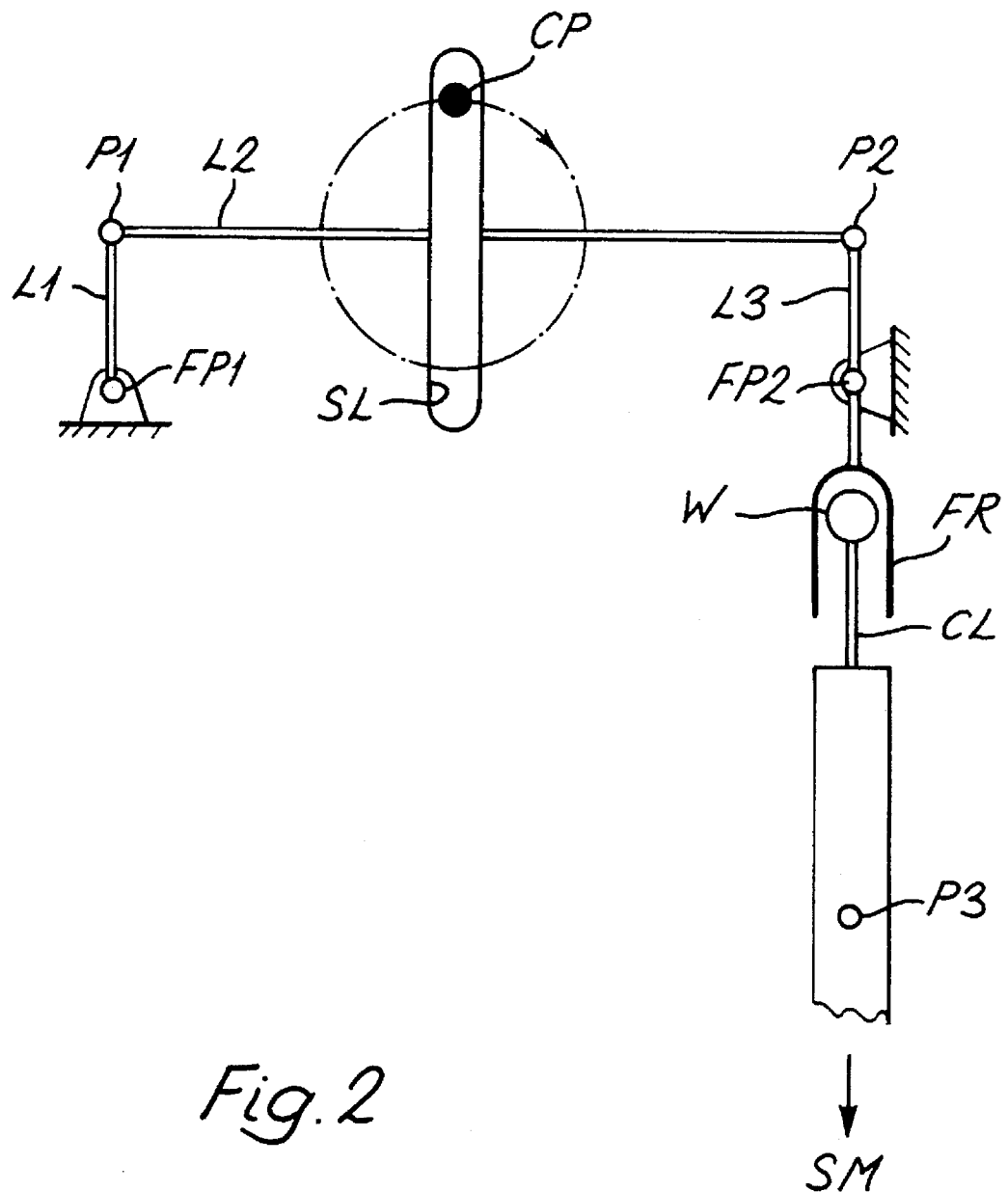
FIG. 2 is an outline schematic drawing of a mirror drive linkage for the scanning apparatus of FIG. 1

FIG. 2 shows a suitable linkage to produce the required movement. An arrangement of three levers L1, L2 and L3 is supported at two fixed pivots FP1, FP2 and joined at pivots P1, P2. Lever L1 extends from pivot FP1 to P1, lever L2 extends from pivot P1 to pivot P2 and lever L3 extends from pivot P2 to pivot FP2. Lever L3 extends to a fork FR. Lever L2 has a central slot SL which receives a crank pin CP. Crank pin CP is driven on a circular path by drive motor DM (FIG. 1). The circular movement of crank pin CP in slot SL moves lever L2 to-and-fro on levers L1 and L3, moving on the fixed pivots. Fork FR Is thus given a to-and-fro motion. Within fork FR is a wheel N carried on a connecting link CL, pivotted at pivot P3, which link carries the mirror SM, and this mirror in turn is given a swinging motion. Drive motor DM is specifically a d.c. motor so that a smooth swinging motion is produced. The tilting motion is step-wise so a stepper motor is suitable. If a stepper motor is used it may be possible to derive adequately accurate information about mirror tilt directly from the drive information for the stepper motor, thus saving a position indicator.

By suitable choice of dimensions the motion of the mirror is sufficiently linear over an adequate swing to produce the scanning action. In FIG. 2:

FP1-P1=FP2-P2=22 millimeters,

FP2-P3=144 millimeters,

CL, from P3 to the center of the wheel 'W', has a length of 132 millimeters, radius of motion of CP=15 millimeters, the scanning angle of mirror SM is about ±6° and the diameter about 150 millimeters in the described embodiment.

Figure 3:
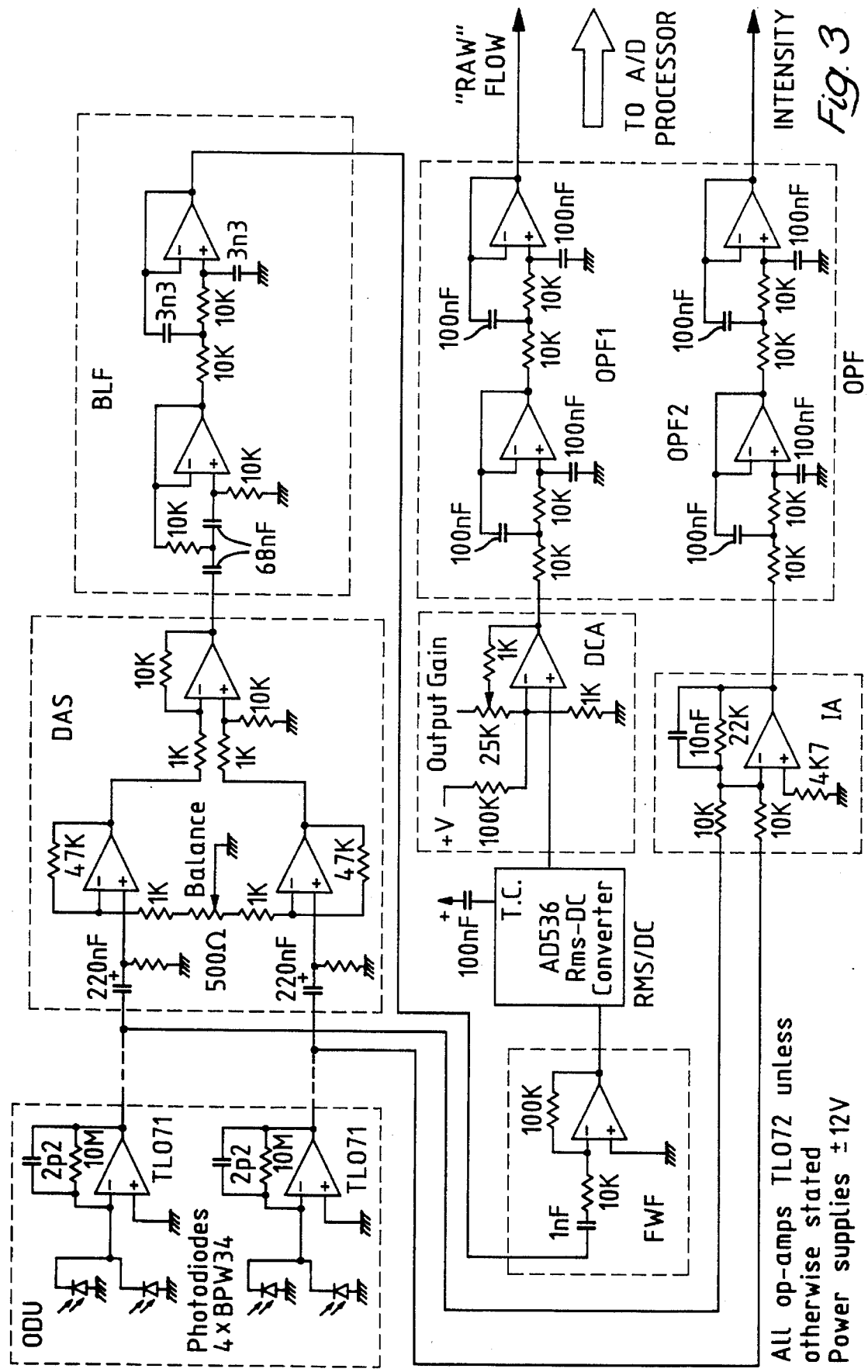
FIG. 3 is an outline schematic circuit diagram.

FIG. 3 shows the circuit diagram for one circuit arrangement for processing the signal from the receiving device.

The component types and values are given in widely-understood nomenclature and by way of example to enable one skilled in the art to produce a suitable circuit with modifications appropriate in a particular embodiment of the invention. Accordingly well-known features such as power supply and constructional techniques will not be described in detail.

A laser power of about one milliwatt is adequate and "intrinsically safe" lasers are suitable. In one embodiment the laser was a Mells Griot Model OSLHR 111 which has a minimum power of one milliwatt and an actual power of about two milliwatts.

As shown in the circuit portion ODU (optical detector unit) the combined outputs from the upper pair of diodes and the combined outputs from the lower pair are taken in parallel to respective amplifiers ODA1, ODA2. This unit is conveniently close to the diodes, which are in a light-tight box. The outputs from these amplifiers are supplied as inputs to respective differential amplifiers DA1, DA2 in circuit portion DAS (differential amplifiers stage). As shown the differential amplifiers are a.c. coupled and have a balance control to permit adjustment to compensate for optical and electrical channel differences. The differential amplifier arrangement provides cancellation of correlated signals which reduces the effect of laser "noise", which is common to both input channels. This also reduces the effect of large changes in signal intensity in passing between light and dark areas on a target during scanning. The scatter-related frequencies of the returned collected light produce an interference pattern in space which is not spatially correlated. The detectors are not at one point in space so their outputs are uncorrelated and are amplified in the circuit. The arrangement thus allows the scatter-related information to pass through as this is uncorrelated.

The output from the differential stage DAS is supplied to a filter (BLF) to limit bandwidth and a filter (FWR) having a frequency weighted response.

The bandwidth filter has the range 230 Hz to 4800 Hz in the arrangement described. Below 230 Hz scanning effect artifacts occur and there are power frequency components at 50 Hz (or 60 Hz) and harmonics, especially 100 Hz (or 120 Hz) from lighting. Above about 5000 Hz the scatter-related spectrum strength is small with respect to circuit noise.

The frequency weighted response filter FWF basically has a response of gain increasing proportionally with frequency over the bandwidth of interest. By about 10,000 Hz the gain has risen to a value of about 10, which does not increase as the frequency increases further.

The r.m.s. to d.c. converter RMS/DC produces an output of a d.c. voltage proportional to the true r.m.s. value of the output waveform from filter FWF. This waveform is the frequency weighted scatter-related spectrum together with circuit noise. The converter output is thus a measure of the power in the spectrum and of the circuit noise. In the d.c. amplifier DCA the 100K resistor to the +12 v line compensates for most of the offset due to circuit noise and gives more effective use of the range of the converter RMS/DC. The output of d.c. amplifier DCA is applied to one of two identical output filters OPF1, OPF2, in this case OPF1. Each filter has a cut-off frequency of 160 Hz to optimize the outputs having regard to the pixel rate. This reduces image noise without unduly affecting resolution.

A further output from the optical detector ODU is supplied through an intensity amplifier IA to the other filter, OPF2.

The output from filter OPF1 can be considered as the "raw" flow signal and includes not only the scatter-related information but also the noise in the detectors and circuit. The shifts in frequency in the scattered light are the result of the Doppler effect on the frequency of the incident light when scattered by a moving object. The relative directions of movement are also significant.

The chief source of noise, shot noise in the photodiodes, is dependent on the intensity of incident radiation. Compensation for this is achieved by determining the relation between intensity of incident radiation and noise power In the flow signal. By illuminating the photodetectors in the absence of the scanning laser with a gradually increasing illumination and noting the "raw" output and the intensity output a correction relationship for use when the photodetectors are used to detect scanned radiation can be produced. A computer can be arranged to determine the correction relationship and apply this to correct the signal in use, as will be understood by those skilled in the art.

Another correction can be made to compensate for the fall-off in signal when scanning at an angle to the surface of a target, such as the corners of rounded targets. As the intensity signal falls the flow signal can be proportionally increased, i.e., by dividing the raw signal by the intensity signal. This correction appears to be reasonably independent of the angle of incidence at the rounded corners.

A typical scanning speed is 5 milliseconds per pixel, where there are 250 pixels per line and 250 lines. At this speed one scan of a target, say a human torso, takes about six minutes. While the target must not move about during this time the arrangement can cope with the normal small movements made by a person sitting on a chair.

Measurements have been made using a test rig to estimate the accuracy of the technique. Over a flow range of 5 to 50 milliliters-per hour a reasonably linear characteristic was obtained, the intensity compensation being used. Measurements also showed that the corner compensation produced satisfactory results.

In the above described embodiment the scanning arrangement can examine a target object about one meter high and half a meter wide placed about two meters away. The "depth of field" is about half a meter at the two meter distance. A field of examination such as this means that a torso or limb can be scanned in one action. Other target sizes and shapes can be handled by suitable and readily-apparent adjustment of arrangement. Smaller and larger targets can be handled and the scan fitted to give an image that fills a display screen.

Some problems arise at the edges of the object if it curves away. However it is possible for a clinician to allow for this in interpreting the image produced, also signal processing can be used to compensate for the effect, as mentioned above.

The techniques described above, by way of non-limiting examples, permit the rapid determination of blood flow in a person without invasion or even contact and will provide considerable assistance to practitioners.

We claim:

1. A method of determination of blood flow to produce a map of said blood flow, said method comprising the steps of:

scanning a rod of laser light in two directions over an area of a surface beneath which area of the surface blood flow in a vessel or vascular bed is to be determined, collecting light returning from the rod of light scattered by the surface and by blood flowing beneath the surface, measuring a spectrum of frequencies in said collected light, determining, from differences in said frequencies in said spectrum, blood flow in a vessel or vascular bed beneath said surface, and producing from said determined blood flow the map of blood flow for a given area of said surface.

2. A method according to claim 1 further comprising the step of:

presenting said determined blood flow as an image of the surface colored or shaded in accordance with a scale of blood flow.

3. A method according to claim 1 further comprising the step of:

providing a reference for the detected frequencies of light returned from the surface for the determination of blood flow beneath the surface.

4. A method of determination of blood flow further comprising the step of:

generating and projecting a rod of laser light, causing said rod of light to scan in two directions over a surface beneath which surface blood flow in a vessel or vascular bed is to be determined, generating rod-motion information related to said moving light rod, collecting light returning from the rod and scattered by the surface and by blood flowing beneath, detecting scatter-related frequencies in said collected light, and determining, from at least said rod-motion information and said detected frequencies, blood flow in a vessel or vascular bed beneath said surface.

5. A method according to claim 4 further comprising the step of:

projecting said rod over a space of two meters to a target surface one meter by half a meter in area.

6. A method according to claim 4 further comprising the step of:

providing from the detected frequencies of light returned from the surface a reference for the determination of blood flow beneath the surface against movement of said surface.

7. A method according to claim 4 further comprising the step of:

causing said rod to move in two substantially mutually perpendicular directions over the surface, and producing from said determined blood flow a map of blood flow for a given area of said surface colored or shaded in accordance with a scale of blood flow.

8. A method according to claim 4 further comprising the step of further comprising the step of:

causing said rod to move over the surface in a raster scan.

9. A method according to claim 4 further comprising the step of:

providing one raster direction scan motion by a smooth linkage drive, and providing another raster direction scan motion by a stepper motion.

10. A method according to claim 4 further comprising the step of:

reflecting the rod in a movable mirror, driving the mirror and smoothly to-and-fro in one direction of the raster and driving the mirror step-wise in another direction between said smooth drives.

11. Apparatus to determine blood flow comprising:

a low-noise laser, means for directing a rod of light from said laser to a target, means for scanning the directed rod over said target in two dimensions, thereby causing said target to return the light, means for collecting light from the rod returned from said target, means for detecting frequencies in said collected light, and means responsive to the action of the means for scanning said rod and to said detected collected light frequencies for determining localized target velocity information related to the scan over the target and for providing said information as a scan-based signal.

12. Apparatus according to claim 11 further comprising means for presenting said scan-based information as an image of localized velocity information for the target.

13. Apparatus according to claim 11 wherein the velocity information is information about blood flow below the surface of the target.

14. Apparatus according to claim 11 wherein the blood flow velocity information is presented as a false-color image of the blood flow in the target.

15. Apparatus according to claim 11 wherein the means for detecting returned light is an array of detectors.

16. Apparatus according to claim 15 wherein the laser rod is arranged to pass through an aperture in the array and then along a path also used for the returned light.

17. Apparatus according to claim 11 wherein the returned light frequencies include those representing overall movement of the target which provide a reference for determination of localized velocity information.

18. Apparatus according to claim 11 wherein the means for scanning the directed rod include means to drive a mirror directing the beam in a steady swinging motion and in a stepwise tilting motion.

19. Apparatus according to claim 15 wherein the detectors are four in number arranged in pairs, the output of detectors in a pair are added to give two combined outputs which are then differenced to provide a signal representing frequencies in said collected light.

* * * * *